(12) United States Patent
Fabian et al.

(10) Patent No.: US 7,177,699 B2
(45) Date of Patent: Feb. 13, 2007

(54) LIFESTYLE MANAGEMENT SYSTEM

(75) Inventors: Willa Fabian, Atlanta, GA (US); David Moore, Ham Lake, MN (US); Hal Kaufman, Minnetonka, MN (US); David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 202 days.

(21) Appl. No.: 10/824,740

(22) Filed: Apr. 15, 2004

(65) Prior Publication Data
US 2004/0199221 A1    Oct. 7, 2004

Related U.S. Application Data

(63) Continuation of application No. 09/944,720, filed on Aug. 31, 2001, now Pat. No. 6,735,479.

(60) Provisional application No. 60/211,410, filed on Jun. 14, 2000.

(51) Int. Cl.
*A61N 1/36* (2006.01)
(52) U.S. Cl. ............................... 607/60; 607/30; 607/32
(58) Field of Classification Search ............... 607/4, 607/5, 9, 32, 60; 128/920–925
See application file for complete search history.

(56) References Cited

U.S. PATENT DOCUMENTS

| | | | |
|---|---|---|---|
| 4,476,868 A | 10/1984 | Thompson | 128/419 PG |
| 5,052,388 A | 10/1991 | Sivula et al. | 128/419 PG |
| H1347 H | 8/1994 | Greeninger et al. | 607/30 |
| 5,441,047 A | 8/1995 | David et al. | 128/670 |
| 5,467,773 A * | 11/1995 | Bergelson et al. | 600/522 |
| 5,544,661 A | 8/1996 | Davis et al. | 128/700 |
| 5,553,609 A | 9/1996 | Chen et al. | 128/630 |
| 5,752,976 A | 5/1998 | Duffin et al. | 607/32 |
| 5,756,941 A | 5/1998 | Snell | 178/18 |
| 5,843,139 A | 12/1998 | Goedeke et al. | 607/32 |
| 5,872,923 A | 2/1999 | Schwartz et al. | 395/200.35 |

(Continued)

OTHER PUBLICATIONS

Stampfer et al., "Primary Prevention of Coronary Heart Disease in Women Through Diet and Lifestyle," *New England Journal of Medicine*, vol. 343, No. 1, p. 16-22 (Jul. 6, 200).

(Continued)

*Primary Examiner*—Carl Layno
(74) *Attorney, Agent, or Firm*—Michael C. Soldner; Girma Wolde-Michael

(57) ABSTRACT

A patient monitoring system in cooperation with IMDs provides information, direction and counseling to patients. Specifically, a combination of lifestyle parameters, such as, for example, diet, exercise, weight, medication and environmental factors such as, for example, temperature, UV factor, pollen count, humidity, air pollution index, are integrated to provide a seamless, comprehensive, chronic monitoring system and support for patients. The system includes a home monitor, IMD, and a remote expert station in operable data communications therebetween. Personal data such as weight, environmental data, food data from refrigerators and pantry, type of exercise equipment, medication, physiologically significant events, physician treatment plan and the like are integrated with IMD data to provide continuous patient care, counseling, consultation and notification. The remote expert station enables doctors and other health care providers to review, monitor current and long-term trends of the patient's health status and dispense clinical care as needed.

12 Claims, 6 Drawing Sheets

U.S. PATENT DOCUMENTS

| | | | |
|---|---|---|---|
| 5,957,861 A * | 9/1999 | Combs et al. | 600/547 |
| 6,134,906 A | 10/2000 | Eastman | 62/331 |
| 6,204,763 B1 | 3/2001 | Sone | 340/568.1 |
| 6,261,230 B1 | 7/2001 | Bardy | 600/300 |
| 6,285,909 B1 * | 9/2001 | Sweeney et al. | 607/32 |
| 6,363,282 B1 | 3/2002 | Nichols et al. | 607/30 |
| 6,398,727 B1 * | 6/2002 | Bui et al. | 600/300 |
| 6,402,689 B1 | 6/2002 | Scarantino et al. | 600/300 |
| 6,442,433 B1 * | 8/2002 | Linberg | 607/60 |
| 6,471,645 B1 * | 10/2002 | Warkentin et al. | 600/300 |
| 6,480,745 B2 * | 11/2002 | Nelson et al. | 607/60 |
| 6,599,250 B2 * | 7/2003 | Webb et al. | 600/483 |
| 6,622,050 B2 | 9/2003 | Thompson | 607/60 |
| 6,805,667 B2 * | 10/2004 | Christopherson et al. | 600/300 |
| 2001/0025137 A1 | 9/2001 | Webb et al. | 600/300 |
| 2002/0019586 A1 * | 2/2002 | Teller et al. | 600/300 |
| 2003/0055406 A1 | 3/2003 | Lebel et al. | 604/891.1 |

OTHER PUBLICATIONS

"Lifestyle, Not Genes, Blamed for Most Cancers," *Minneapolis Star & Tribune*, p. A8-9 (Jul. 13, 2000).

Lichtenstein et al., "Environmental and Heritable Factors in the Causation of Cancer—Analyses of Cohorts of Twins from Sweden, Denmark, and Finland," *New England Journal of Medicine*, vol. 343, No. 2, p. 78-85 (Jul. 13, 2000).

Nabel, "Coronary Heart Disease in Women—An Ounce of Prevention," *New England Journal of Medicine*, vol. 343, No. 8, p. 572-4 (Aug. 24, 2000).

* cited by examiner

LIFESTYLE MANAGEMENT SYSTEM

The following is a continuation of application Ser. No. 09/944,720, now U.S. Pat. No. 6,735,479, filed Aug. 31, 2001, and which claims priority filing based upon U.S. Provisional Application No. 60/211,410, filed Jun. 14, 2000.

FIELD OF THE INVENTION

The present invention generally relates to medical devices and communications systems. Specifically, the invention relates to a method and apparatus that allows a patient to manage and positively affect the onset, time course and severity of various disease conditions. The invention includes an implanted medical device that provides patient data to a home monitoring system, which also has various additional inputs to improve and modify the patient's environment and life style. The patient's implanted device, home monitoring system, and a remote expert station maintain data communication via standard telemetry systems, home network systems such as Bluetooth, HomeRF, or WLAN, and the Internet, worldwide web, intranet, extranet, cellular, or other similar network or communication systems.

BACKGROUND OF THE INVENTION

Lifestyle and environmental factors are major impactors of disease progression, remission, and even onset. For example in "Primary Prevention of Coronary Heart Disease in Women through Diet and Lifestyle", Stamper, et al, New England Journal of Medicine, Vol 343, No 1, Jul. 6, 2000, pg 16–22 found that 82% of coronary artery disease is attributed to a lack of adherence to a low risk lifestyle (such as, diet, moderate exercise and abstinence from smoking). Additionally, in "Environmental and Heritable Factors in the Causation of Cancer—Analyses of Cohorts of Twins from Sweden, Denmark, and Finland", Lichtenstein, et al, New England Journal of Medicine, Vol 343, No 2, Jul. 13, 2000, pg 78–85 found that in a study of twins "inherited genetic factors make a minor contribution to susceptibility to most types of neoplasms" and that "the environment has the principal role in causing sporadic cancer". Lastly, in "Coronary Heart Disease in Women—An Ounce of Prevention", Nabel, New England Journal of Medicine, Vol 343, No 8, Aug. 24, 2000, pg 572–4 found that "lifestyle related risk factors—specifically, smoking, overweight, lack of exercise and poor diet—(increased) the risk of coronary artery disease". Women who had none of the risk factors had an 83% reduction in coronary events than the women with one or more risk factors.

We propose that by providing feedback and consoling to patients with implantable medical devices (IMDs, i.e., PCD, pacemaker, neurostimulator, drug pump, ILR, Chronicle monitor, etc.), we can impact environmental factors, diet, exercise level, medicant intake adherence, etc., and provide a substantial proactive, preventative positive impact on the onset, progression and quality of life of many types of cardiac and heart failure patients. Additionally, non-implanted patients may also greatly benefit from this system because the system is adaptable to be used as a preventative tool for those most susceptible to diseases (through heredity, work environment, etc.) or in the beginning stages of a progressive disease.

The concept of home health care began in the 1850's when traveling health care professionals, usually physicians, provided in-home visits to those who were in need of health care and unable to seek such care outside of the home. From the outset, however, traveling between various patients' homes constituted "downtime" for the health care professional. In the middle of the twentieth century, this type of medical service was transferred from the physician to nurses or other health care workers. During the past decade, providing home health care has become more difficult due to the shortage of health care professionals in general and, in particular, of those who provide home health care. Because of this shortage as well as the increase in medical costs, home health care visits are generally limited to basic needs of the most ill patients and/or medical emergencies.

On the other hand, the number of patients who are home bound has been increasing. Many terminally ill patients, such as heart failure or cancer patients among others, are sent home to live with their families who provide 24-hour in-home care. Other patients with chronic health problems reside in their homes where they receive necessary support and treatment on an "as needed" basis. Through the auspices of hospices or other support groups, nurses or health care workers provide medical care and evaluation on a periodic basis—usually a ½ hour visit once or twice a week. Although these visits provide the contracted services, nonetheless they suffer from minimal oversight of a physician-ordered treatment and/or preventative plan.

Additionally, with longevity increases of the past several decades, more elderly people are living longer and developing disease states that are initiated or made more pronounced by the environmental conditions as stated in the herein above listed articles. The ill elderly are often given a treatment plan by their physician that can positively impact their longevity and quality of life if followed correctly and religiously. Often a spouse or adult children must monitor, administer and console the patient's adherence to this plan of treatment. This manual, ad hoc process often is time consuming, confusing, prone to errors and not well administered in many cases.

Patients with implantable medical devices (IMDs) also require regular checkups to determine whether their IMDs have been functioning properly. Most patients with IMDs must be monitored bi-annually, at the very least. Such monitoring may occur transtelephonically from the patient's home or via telemetry as has been disclosed in U.S. Pat. No. 5,752,976 issued to Duffin, et al, "World Wide Patient Location and Data Telemetry System for Implantable Medical Devices", incorporated herein by reference in its totality. The '976 patent however does not describe a system that provides automatic feedback to a patient to reinforce positive activities and monitor adherence to a physician ordered treatment regime.

Various solutions to these issues, in addition to the '976 patent, have been suggested in the art. U.S. Pat. No. 5,553,609 issued to Chen, et al, "Intelligent Remote Visual Monitoring System for Home Health Care Service" discloses a computer-based remote visual monitoring system connected transtelephonically to a remote master-monitoring computer. This system is intended for use by a visiting nurse during an in-home patient health care visit. Separate audio and visual equipment facilitates communication between the patient's home and a remote station. The '609 patent, however, does not teach a method for continuous monitoring, treatment adherence and consoling patients with IMDs.

A remote visual monitoring system for home health care is disclosed in U.S. Pat. No. 5,553,609 issued to Chen, et al, "Intelligent Remote Visual Monitoring System for Home Health Care Service". The system has several layers, including units in the patient's home, the caregiver's office, and the supervisory control center. Audiovisual equipment in the patient's home and at the caregiver's office provides two-way communications during a home visit. There is also a provision for generating and maintaining the patient's medical records. U.S. Pat. No. 5,872,923 issued to Schwartz, et al, "Collaborative Video Conferencing System" discloses a video conferencing system, wherein multiple parties at different locations can view, and modify, a common image on their computer displays. The invention also provides a video camera at each computer, which takes a video picture of each party. The systems described in the '609 and '923 patents, however, do not provide for continuous monitoring, treatment adherence and consoling patients with IMDs.

What is needed is a system that provides guidance, monitoring, and feedback to a patient to follow a suggested treatment or therapy plan by his/her physician to allow life style changes that will positively affect their disease onset and/or progression and associated medical problems.

SUMMARY OF THE INVENTION

The present invention enables the capture of non-technical, health-related, exercise activities, food and medicant intake and environmental information through various automatic computerized means and to be displayed in conjunction with, or overlaid upon, implantable medical device (IMD) derived information. Trends of lifestyle data may be analyzed through a graphically displayed calendar view combined with device information allowing the patient and their physician the ability to monitor adherence to exercise and diet treatment regimes prescribed by the physician. Further, the invention enables cardiac arrhythmia, heart failure, cancer, lupus, hypertension, and the like patients to alter their lifestyle in a continuous, chronically supportive manner. This concept would also allow proactive, preventative lifestyle changes to high-risk patients to potentially prevent, reduce and/or delay major medical problems.

DETAILED DESCRIPTION OF THE DRAWINGS

Figure 1:
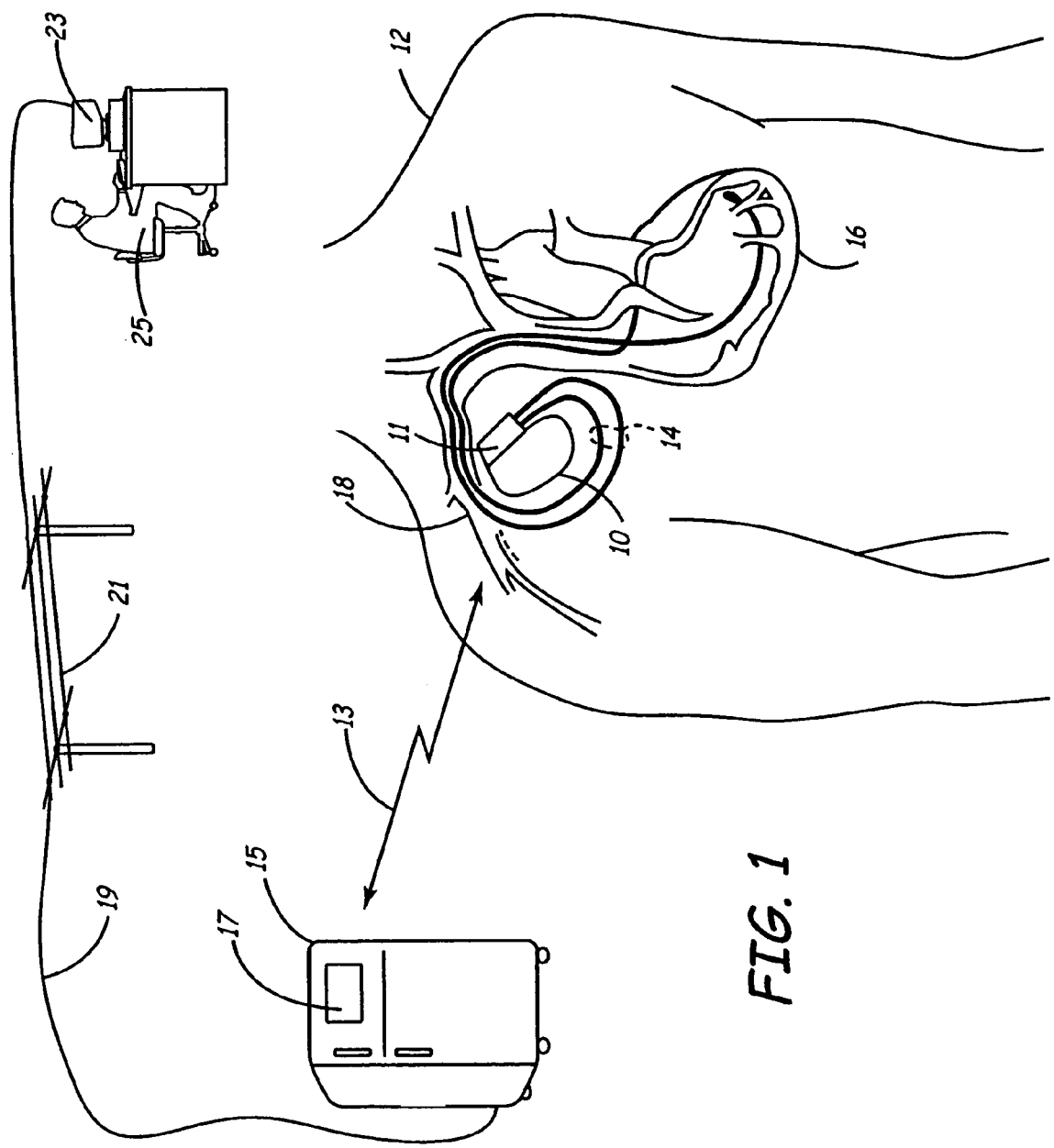
FIG. 1 is an illustration of a body implantable device system in accordance with the present invention, including a hermetically sealed device implanted in a patient, an external patient display and remote monitoring system.

FIG. 1 is an illustration of an implantable medical device system adapted for use in accordance with the present invention. The medical device system shown in FIG. 1 includes implantable device 10—a pacemaker for illustration purposes—that has been implanted in patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16.

The present invention will be described herein in an embodiment that includes a pacemaker. Those of ordinary skill in the art, however, with the benefit of the present disclosure will appreciate that the present invention may be advantageously practiced in connection with numerous other types of IMDs such as defibrillators, cardioverters, neurostimulators, insertable loop recorders (ILR) such as the Medtronic Reveal, heart failure monitors such as the Medtronic Chronicle, and the like. Also depicted in FIG. 1 is an external patient monitor unit 17 for non-invasive communication with implanted device 10 via an uplink and downlink communication channel 13, to be hereinafter described in further detail. External patient monitor unit 17 is shown incorporated in a refrigerator 15 as one exemplary embodiment and as substantially described in U.S. Pat. No. 6,134,906 "Refrigerator with Video Monitor Workstation" by Eastman incorporated herein in its entirety by reference. The '906 patent describes a video monitor attached to a refrigerator for combining visual graphic display with the functional capability to store and access refrigerated products. Near continuous workstation operation can be conducted while permitting access to refrigerated food and beverage products. Access to the refrigerator interior can be made through a moveable video screen or through a side door. A controller can be engaged with the video monitor for transmitting graphic data, and a keyboard can provide interactive control over the displayed information.

Further referring to FIG. 1, patient monitor 17 is additionally connected via an inhome cable 19 and a standard phone line connection 21 to a remote monitor 23 observable via a physician or nurse practitioner 25. Alternatively, this remote connection may be via an ISDN line, cable modem, wireless, cellular, fiber optic cable, or the like. The in-house connection 19 may alternatively be HomeRF, Bluetooth, 802.11, infrared, WLAN or the like. Data transmitted to and from the patient monitor 17 may be encrypted for patient anonymity via methods as described in co-pending application Ser. No. 09/821,518, "Variable Encryption Scheme for Data Transfer Between Medical Devices and Related Data Management Systems", filed Mar. 30, 2001.

Figure 2:
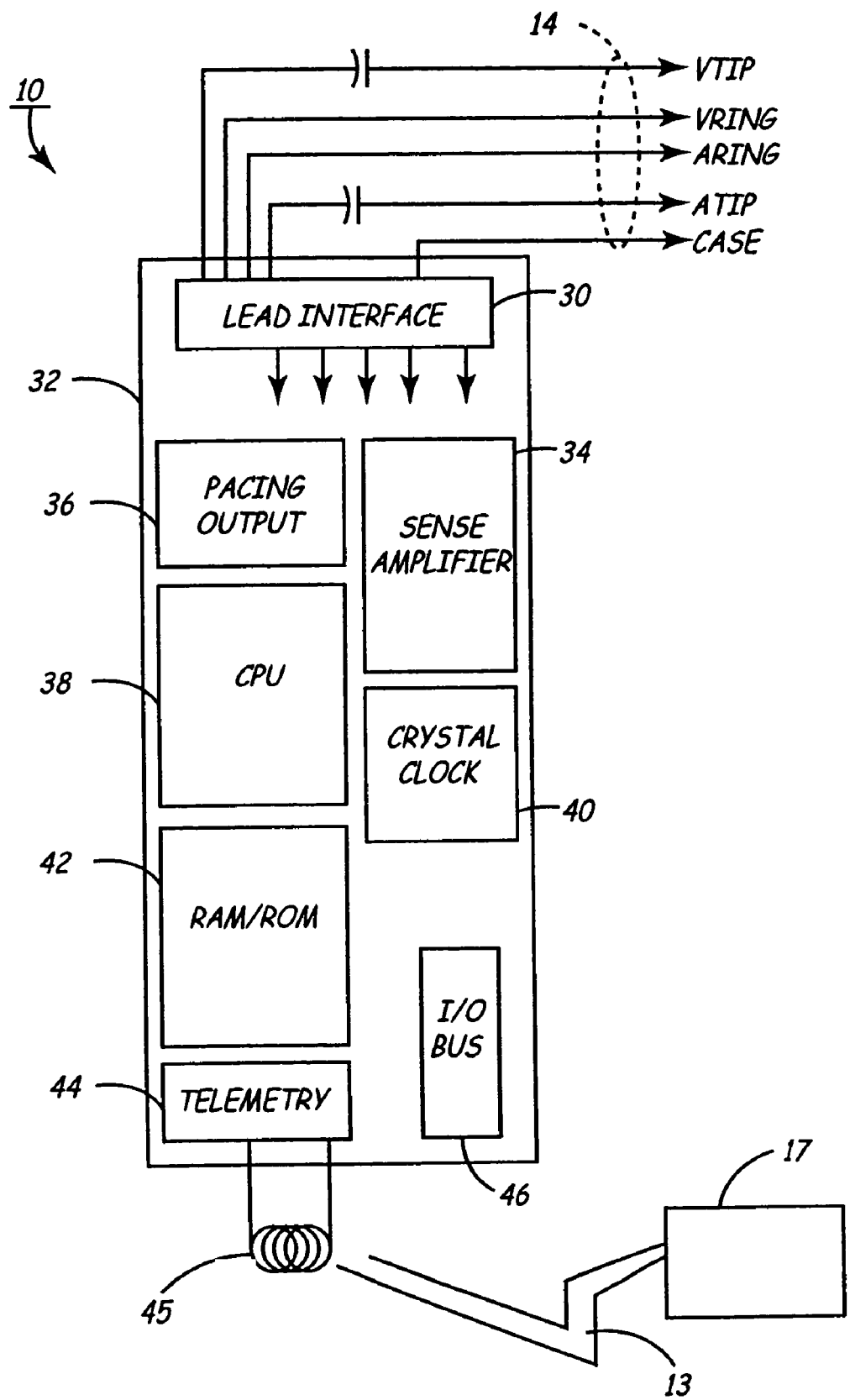
FIG. 2 is a block diagram of the implanted device from FIG. 1.

FIG. 2 is a block diagram of the electronic circuitry that makes up pulse generator 10 in accordance with the present invention. As can be seen from FIG. 2, pacemaker 10 comprises a primary stimulation control circuit 32 for controlling the device's pacing and sensing functions. The circuitry associated with stimulation control circuit 32 may be of conventional design, in accordance, for example, with what is disclosed in U.S. Pat. No. 5,052,388 issued to Sivula et al. To the extent that certain components of pulse generator 10 are conventional in their design and operation, such components will not be described herein in detail, as it is believed that design and implementation of such components would be well known to those of ordinary skill in the art. For example, stimulation control circuit 32 in FIG. 2 includes sense amplifier circuitry 34, stimulating pulse output circuitry 36, a crystal clock 40, a random-access memory and read-only memory (RAM/ROM) unit 42, and a central processing unit (CPU) 38, all of which are well-known in the art. Pacemaker 10 also includes internal communication circuit 44 so that it is capable of communicating with patient monitor device 17.

With continued reference to FIG. 2, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 30 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 2, although it will be clear to those of ordinary skill in the art that, for example, leads 14 will necessarily be coupled, either directly or indirectly, to sense amplifier circuitry 34 and stimulating pulse output circuit 36, in accordance with common practice, such that cardiac electrical signals may be conveyed to sensing circuitry 34, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 32 includes central processing unit 38 which may be an off-the-shelf programmable microprocessor or micro controller, but in the present invention is a custom integrated circuit. Although specific connections between CPU 38 and other components of stimulation control circuit 36 are not shown in FIG. 2, it will be apparent to those of ordinary skill in the art that CPU 38 functions to control the timed operation of stimulating pulse output circuit 36 and sense amplifier circuit 34 under control of programming stored in RAM/ROM unit 42. It is believed that those of ordinary skill in the art will be familiar with such an operative arrangement.

With continued reference to FIG. 2, crystal oscillator circuit 40, in the preferred embodiment a 32,768-Hz crystal controlled oscillator, provides main timing clock signals to stimulation control circuit 32. Again, the lines over which such clocking signals are provided to the various timed components of pulse generator 10 (e.g., microprocessor 38) are omitted from FIG. 2 for the sake of clarity.

It is to be understood that the various components of pulse generator 10 depicted in FIG. 2 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 36, which functions to generate cardiac stimuli under control of signals issued by CPU 38, may be, for example, of the type disclosed in U.S. Pat. No. 4,476,868 to Thompson, entitled "Body Stimulator Output Circuit", which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 34, which is of conventional design, functions to receive electrical cardiac signals from leads 14 and to process such signals to derive event signals reflecting the occurrence of specific cardiac electrical events, including atrial contractions (P-waves) and ventricular contractions (R-waves). Sense amplifier circuit 34 provides these event-indicating signals to CPU 38 for use in controlling the synchronous stimulating operations of pulse generator 10 in accordance with common practice in the art. In addition, these event-indicating signals may be communicated, via uplink transmission 13, to patient monitor device 17 via telemetry coil 45. Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of the patient monitoring and consoling device 17, an associated communication system and a remote observation device 23.

Figure 3A:
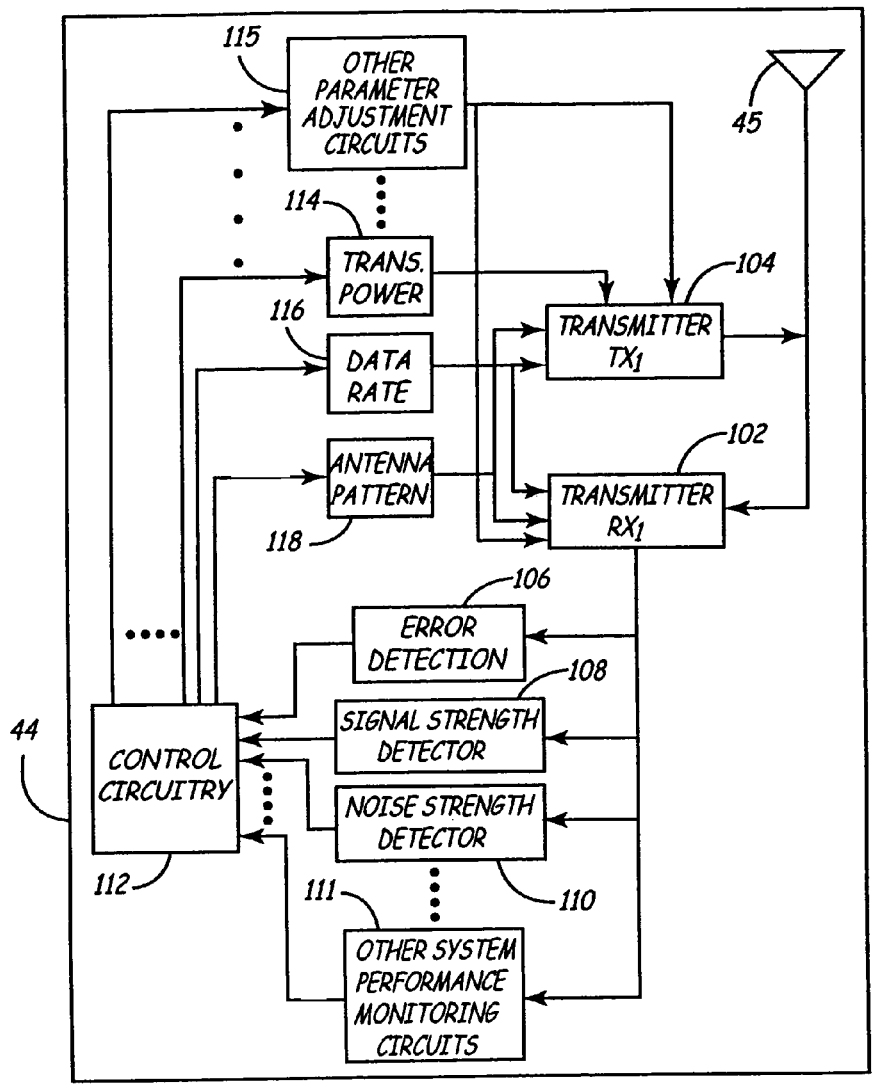
FIG. 3a is a block diagram showing the communication system in accordance with the present invention from the implanted device of FIG. 2.

Turning now to FIG. 3*a*, there is shown a simplified block diagram of communication subsystem 44 from pacemaker 10, in accordance with the present invention. Communications subsystem may be, for example, of the type disclosed in U.S. Pat. No. 5,843,139 to Goedeke, et al., "Adaptive Performance-Optimizing Communication System for Communicating With an Implanted Medical Device", which patent is incorporated by reference herein in its entirety.

Communication subsystem 44 in implantable device 10 includes a receiver 102 and a transmitter 104 each coupled to antenna 45 (FIG. 2) which may be implemented as a multiple-turn wire coil, a stub wire, or a pacing lead. Communication subsystem 44 further includes, in one embodiment, error detection circuitry 106, signal strength detection circuitry 108, and noise strength detection circuitry 110. Generally speaking, error detection circuit 106, signal strength detection circuit 108, and noise strength detection circuit 110, can be called system performance monitoring circuits which function, as that name suggests, to dynamically monitor one or more aspects of communication system 44. Error detection circuit 106, for example, may utilize well-known error detection techniques to determine the bit error rate (BER) and the SNR of digital information received by receiver 102. Signal strength detector circuit 108 may effectively consist of a logarithmic amplifier that detects and filters the RF signal (or IF signal if downconverted) to provide an RSSI (received signal strength indicator) output that gives a voltage proportional to the logarithm of the signal strength at the receiver's RF input. Detector 108 will only respond to the signal present within the receiver pass band. In this way, the desired signal strength (actually, signal plus noise) can be measured. Likewise, the noise can be measured with the same apparatus under the condition of a known period with no received transmission. In this way the signal-to-noise ratio of the received signal can be measured by a simple comparison of the signal and the noise RSSI samples. This method, as would be appreciated by those of ordinary skill in the art, would effectively implement circuit 110 as well as 108 in FIG. 3*a*.

With continued reference to FIG. 3a, circuits 106, 108 and 110 are in turn coupled to a control circuit 112 that, in one embodiment, may be a custom integrated circuit or the like. Control circuit 112 in communication subsystem 44 functions to control various aspects of communication operation in device 10, and further functions to cause data to be transmitted to patient monitor and display device 17 (FIG. 1). For example, as shown in FIG. 3a, control circuit 112 is coupled to a transmitter power control circuit 114, such that under command of control circuit 112, the power of signals transmitted by transmitter 104 can be adjusted up or down. Similarly, control circuit 112 is coupled to a data rate control circuit 116 that controls the rate at which data is transmitted from transmitter 104. Control circuit 112 is also coupled to an antenna pattern (field strength as a function of position) control circuit 118, so that the antenna pattern for reception and transmission of transmitted signals may be dynamically configured during operation of communication subsystem 44 and to receiver circuit 102 so that the bandwidth of the bandpass filter therein may be adjusted.

Figure 3B:
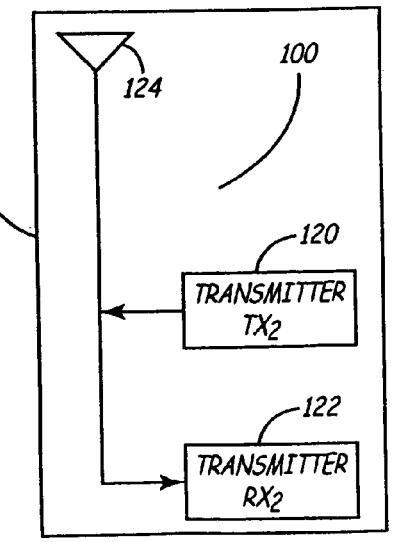
FIG. 3b is a block diagram showing the communication system in accordance with the present invention from the patient monitor of FIG. 1.

Control circuit 112 is responsive to prioritized sets of operational goals to be accomplished in conjunction with each of a plurality of telemetry transmission types, stored in RAM/ROM 42 (FIG. 2). In response to an identification of the type of telemetry to follow, processor 38 (FIG. 2) instructs control circuit 112 as to operational parameters and through control circuitry 112 monitors the outputs of the performance monitoring circuits 106, 108, 110, 111. Under control of processor 38, control circuitry adjusts the various parameter adjustment circuits to achieve the operational goals stored in RAM/ROM 42, in order of their priorities. Control circuitry 112 in some cases adjusts the operational parameters associated with transmitter 104 or receiver 102. Alternatively, parameter adjustment commands may be formatted by processor 38 for transmission by transmitter 104 to receiver 122 (FIG. 3b), to control corresponding parameter adjustment circuits associated with transmitter 120 (FIG. 3b).

In accordance with an important aspect of the invention, communication subsystems 44 and patient monitor device 17 (FIG. 3a) are preferably capable of exchanging information with each other, such that IMD 10 can transmit, upon command, its stored data related to operational parameters to patient monitor device 17. For example, if signal strength detector circuit 108 in subsystem 44 determines that the received signal transmitted from transmitter 120 is unacceptably weak, control circuitry 112 can initiate transmission of a command to subsystem 100 instructing transmitter 120 to increase its transmission power.

In accordance with one aspect of the present invention, the performance goals of the communication system, and the standards or limits imposed upon operational parameters, may themselves be adjusted on a dynamic basis. Then, it would be desirable to increase the minimum transmission range to be maintained by the communication system, so that patient monitor device 17 can establish telemetric communication with the patient's implanted device from a longer-than-normal distance, e.g., from bedside or even across the room.

Typically a telemetry system employing the present invention will include a plurality of performance goals applicable in conjunction with each of a variety of telemetry transmission types. In most cases it is envisioned that the performance goals will include one or more absolute requirements for a transmission to be considered acceptable. For example, in most cases a maximum error rate will be the highest priority performance goal, with acceptable error rates differing based on the telemetry type. For example, in the case of downlink of a command to transmit from patient monitor device 17 to implanted device 10, the acceptable error rate would typically be lower than for an uplink of stored electrogram data from implanted device 10 to patient monitor device 17. Similarly, the performance goal of second priority may differ between two such telemetry transmission types.

The above disclosure assumes that, during initiation of the telemetry link, initial communication between the devices may occur using a telemetry transmission protocol determined to be acceptable for transmission of control signals between the devices, as verified by return transmissions, and that this initial communication will establish the type of telemetry transmission to follow. This protocol may also be used in conjunction with adjustments of the performance parameters, as discussed above. However in many cases, feedback from the receiver to the transmitter is not required to indicate failure of the telemetry protocol in effect to meet the performance parameters. In the case of a transmitted electrogram, implanted device 10 may simply decrease the transmission rate until the minimum transmission rate is reached and thereafter increase power until either a specified maximum power level is reached or until a return transmission from patient monitor device 17 indicates an acceptable error rate.

One class of RF transmission systems for which the present invention is believed to be particularly advantageous is referred to as impulse radio, a technology based upon the pulse position modulation of very low duty-cycle, ultra-wide-bandwidth RF pulses. Impulse radio (IR) pulses are processed with data encoding and pseudo-random noise encoding to smooth the energy in the frequency domain and provide channelization.

FIG. 3b is an even more simplified block diagram of a communication subsystem 100 associated with patient monitor device 17. Communication subsystem 100 is preferably in agreement with communication subsystem 44 in implanted device 10 and as described herein in the above referenced Goedeke '139 patent. For simplicity in FIG. 3b, however, only a transmitter 120, receiver 122 and antenna 124 from communication subsystem 100 are represented in FIG. 3b.

The present invention allows the capture of non-technical, health-related information through various computerized means (Web-based Calendar software, hand-held personal digital assistants (such as the Palm Pilot, Visor, cellular phones WAP, access to the Web-site hosting their device information) to be displayed in conjunction with or overlaid upon the uplinked diagnostic information/data from IMD 10. Such data might include an ECG tracing, stored diagnostic data, pH, arrhythmic events, mean heart rate, mean respiration rate, minute ventilation, or current IMD settings from a pacemaker; or, alternatively, chronic pressure or oxygen signal levels from a heart failure monitor such as the Medtronic Chronicle, among others. The heart failure monitor may be as described in U.S. patent application Ser. No. 09/809,915 "Heart Failure Quick Look Summary for Patient Management Systems" filed Mar. 16, 2001 and incorporated herein by reference in its entirety.

The health related information includes exercise data (type, duration, date, time), sleep schedule, special events (celebratory events, stressful events—weddings, babies, birthdays, parties, etc.) and diet information. Food data is automatically linked to calorie, vitamin and mineral data per a physician recommended diet. Physical activity levels are linked with additional device information such as EKG, BPM, and blood pressure from interrogation of the implanted device. Trends of lifestyle data are analyzed through a graphically displayed calendar view combined with device information allowing the patient and their physician a biofeedback loop to indicate what events in the patient's life trigger physiological responses (nausea, dizziness, rapid heart rate, high BP, weight gain or loss, etc.). Positive events and negative events are monitored for impact and possible lifestyle changes. Capture of exact mental and physical environments at the time of device triggered events are stored so that the physician would have complete information to determine lifestyle influences on device activated responses (see FIG. 6 as a representative example).

This invention additionally uses the concept of automatic Internet ordering of food items via RF UPC labels (in conjunction with Internet based appliances) to provide visual and or verbal feedback to a patient action (i.e., taking drink/food item from refrigerator or pantry, etc), a patient's environment (i.e., temperature, pollen count, humidity, air pollution index, sun (uv index), a patient's activity level (from interrogation of implanted device (i.e., long term activity, short term activity, time of day, etc)), and the patient's physician treatment plan (i.e., weight loss/maintenance, type of food (i.e., low sodium diet), liquid intake, time of day, medicants, etc). The RF UPC code allows the amount of food, the type of food, and the constituents of food (i.e., sodium, calories, vitamin A and C, total fat content, saturated fat, sugar, protein, dietary fiber, carbohydrates, cholesterol, calcium, iron, serving size, etc.) to be monitored and positive/negative feedback and/or consoling provided. The above information may be used to positively impact the day to day lifestyle and environment of many types of patients with such maladies as CHF, overweight (obesity), cancer, lupus, cardiac disease, emphysema, and the like.

Figure 4:
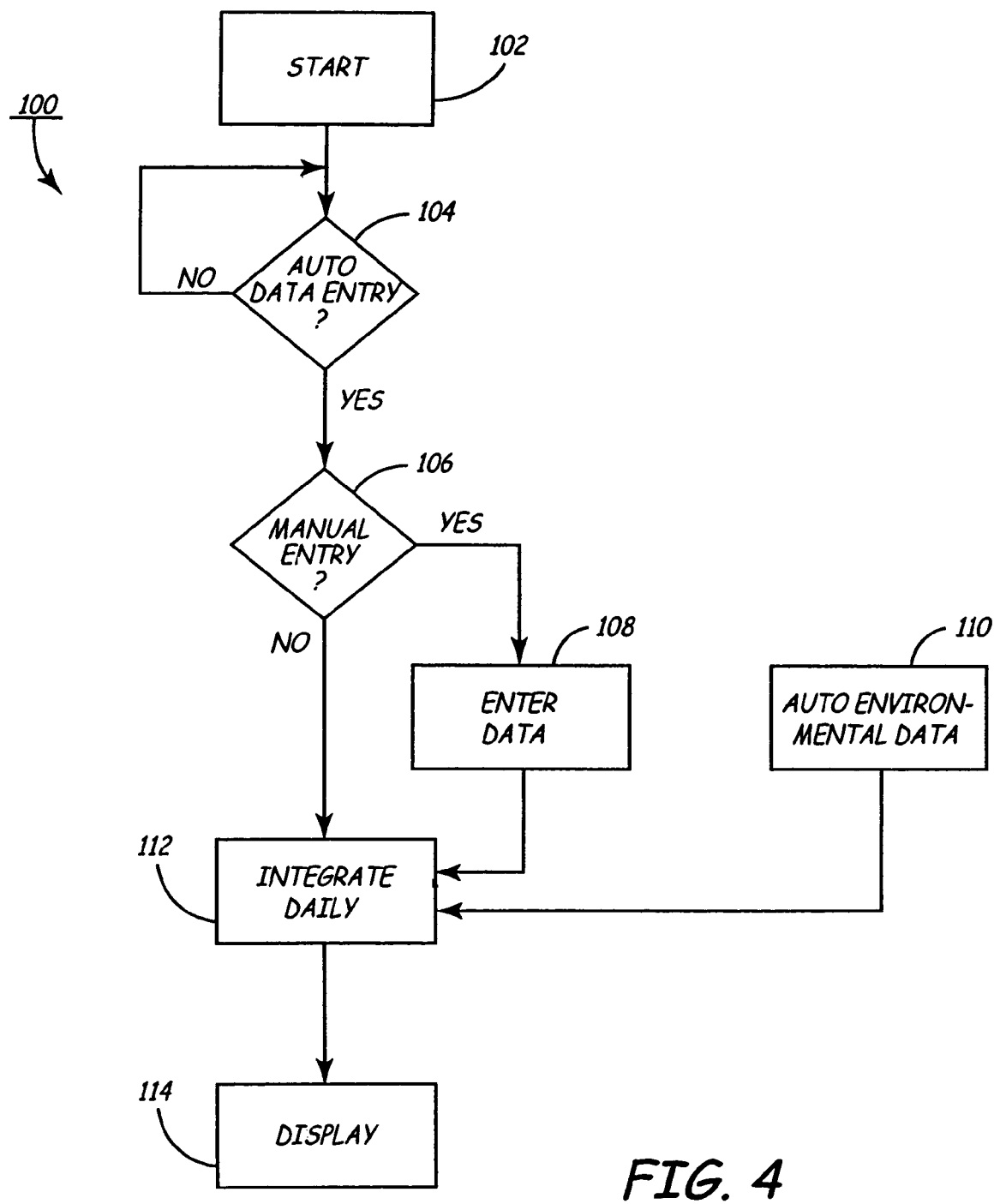
FIG. 4 is a flow diagram showing one aspect of the present invention.

Turning now to FIG. 4, a flow diagram 100 of the present invention is shown. At block 104, the system waits in a loop for automatic data entry from the refrigerator, pantry, medicant delivery system, weight from a scale, blood pressure measurement, exercise data (time, amount of effort, etc. from treadmill, stair climbing, walking, jogging, cycling, swimming, and/or skating) and the like. The patient may enter data on their daily activities (exercise, mental state, sleep schedule), any significant medical events (dizziness, nausea, rapid heart rate), medical data (weight, glucose measurement, etc.) and the like at step 106. Inputting data may be accomplished via a digitizer pen, tethered to the patient monitor display 17, for example, as disclosed in U.S. Pat. No. 5,756,941, issued to Snell "Retractable Pen Tether for a Digitizer Pen and Method of Attaching a Digitizer Pen to a Digitizer", incorporated herein by reference in its totality. Such a pen is intended for use in a hand-held computer and is kept in a pen storage chamber incorporated within the body of the typical PDA. Such digitizer pens, though not tethered to the PDA as taught by the '941 patent, are now commonly available with commercial PDAs. Such common use should make these digitizer pens an easy-to-use tool for the patient. Alternatively, voice entry may be used by the patient to enter data on their daily activities. The automatic and annually entered data is integrated at step 112. Additionally, at step 110, environmental data such as temperature, pollen count, uv index, humidity, and the like may be automatically downloaded from various weather sources accessible by the Internet. The data is displayed to the patient on the patient monitor 17 or, alternatively, verbally conveyed to the patient at step 114 with recommendations, consoling, and status. This information may also be transmitted via a standard phone connection and modem or the Internet to the patient's following physician for his review and consoling of the patient.

Figure 5:
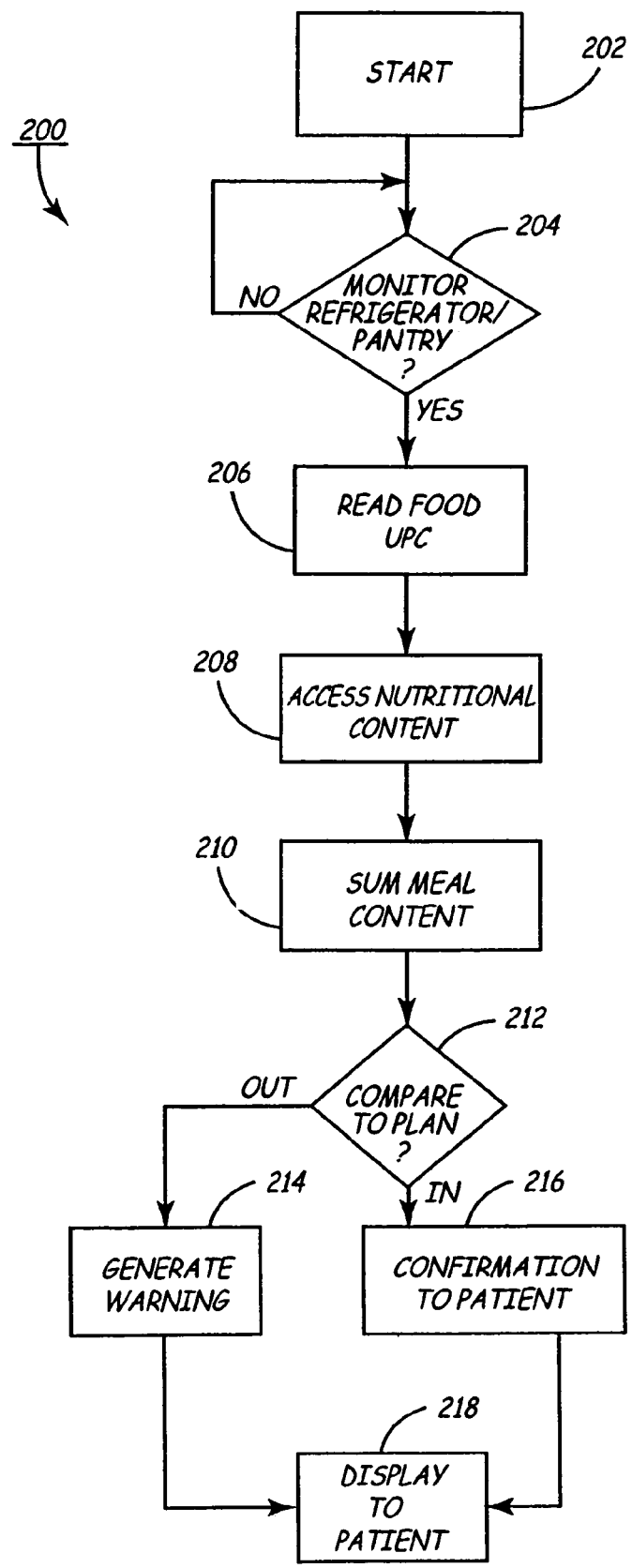
FIG. 5 is a flow diagram showing a further aspect of the present invention.

Turning now to FIG. 5, a further flow diagram 200 of the present invention is shown. At step 204, the system waits in a loop for automatic data entry from the refrigerator, pantry, or other food storage location. Upon removal from the storage device (refrigerator or pantry) of a food item by the patient, the food Universal Product Code (UPC) is read 206 to identify the type and container size removed. The UPC code may be read by interrogation of a RFID insert or tag as provided by Intelitag from Intermec Technologies. This is a passive insert or tag attached to a food item that may be read by a proximity interrogator typically designed for interrogation at 915 to 2450 MHz. Alternatively, the weight of various foodstuffs may be monitored to provide the input for the present invention, for example, in accordance with U.S. Pat. No. 6,204,763 "Household Consumable Item Automatic Replenishment System Including Intelligent Refrigerator" to Sone is incorporated herein by reference in its entirety. The '763 patent describes a household consumable item automatic replenishment system that automatically maintains a desired inventory of household consumable items. The household consumable item automatic replenishment system has a refrigerator compartment having an indoor access and an outdoor access and an unrefrigerated compartment having an indoor access and an outdoor access. An automatic inventory system has a plurality of sensors configured to provide information representative of an inventory of the refrigerated compartment and the unrefrigerated compartment. An inventory processor is coupled to the sensors to process the information representative of the inventory of the refrigerated compartment and the unrefrigerated compartment, so as to make a list of items which are to be replenished. An automatic ordering system comprises a telecommunications device coupled to cooperate with the inventory processor to communicate at least a portion of the list to at least one vendor.

Further referring to FIG. 5, at step 208 the patient monitor accesses the nutritional content of the foodstuff removed and to be consumed. The program sums at step 208 the meal content from the various containers removed at step 208. At step 212, the meal content is compared to a plan of treatment and therapy provided by the patient's doctor. If some content is out of the planned range, a warning is provided to the patient at step 214 and displayed to the patient at step 218. If the meal content is within the plan, a confirmation is provided to the patient at step 216 and displayed at step 218. This information may also be transmitted via a standard phone connection and modem or the Internet to the patient's following physician for his review and consoling of the patient.

Figure 6:
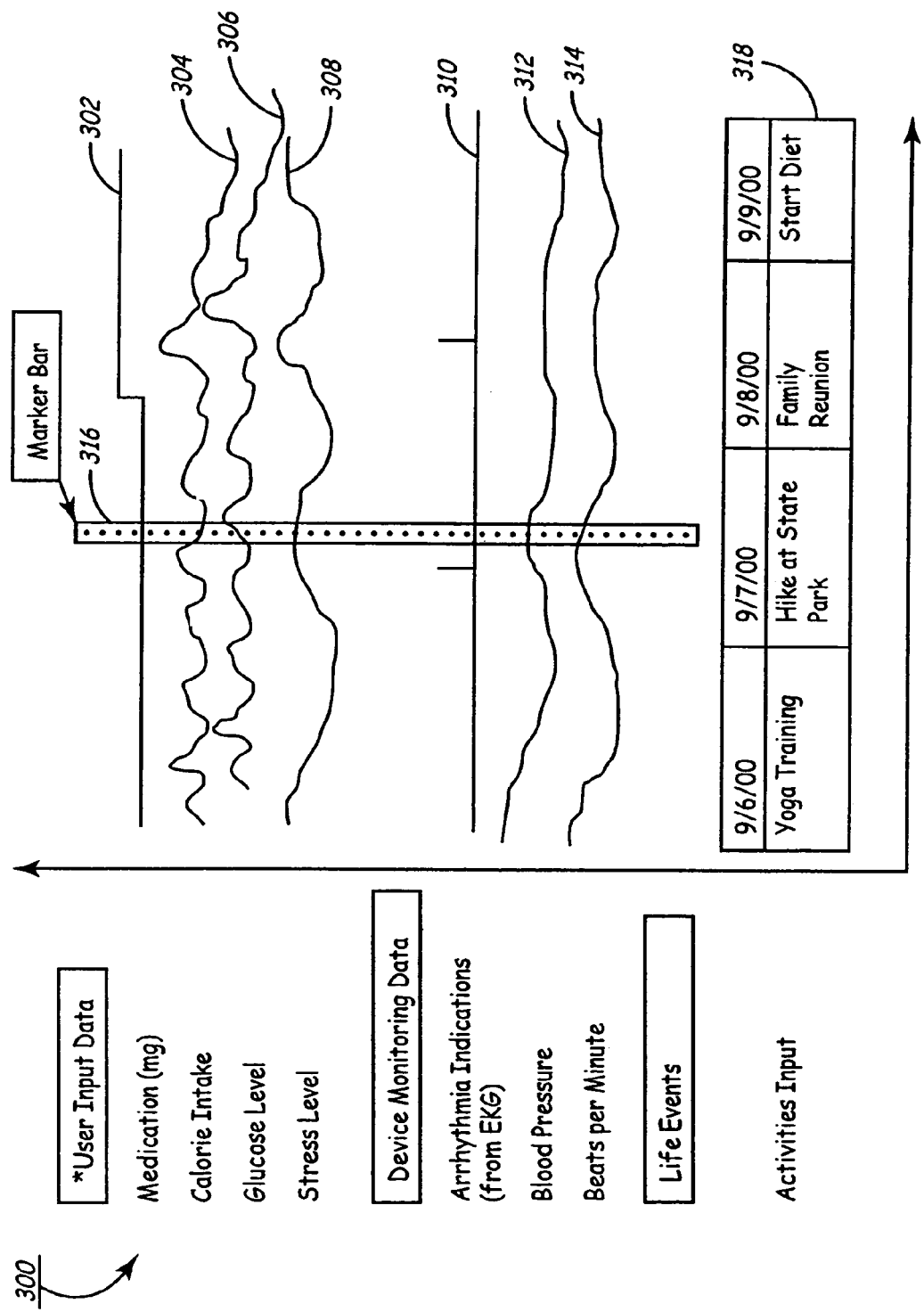
FIG. 6 is a Lifestyle Management Trend Chart for providing information to the patient and his/her following physician.

FIG. 6 shows an example of a lifestyle management trend chart 300 that shows daily, weekly, monthly, or even yearly trend information from various parameters (302–314) that are selectable by the monitoring physician for monitoring the patient's progress or providing feedback to the patient. Life events such as recreational activities and significant events 318 are also shown. A marker bar 316 may be moved horizontally to allow visualization of the correlation between various environmental inputs, exercise activities, food intake, medicant ingestion, and the like and their impact on a physiologic variable/parameter and/or patient well-being.

The preceding specific embodiments are illustrative of the practice of the invention. This invention will allow cardiac arrhythmia, heart failure, cancer, lupus, hypertension, and the like patients to alter their lifestyle in a continuous, supportive manner. This concept would also allow proactive, preventative lifestyle changes to high-risk patients to potentially prevent, reduce and/or delay major medical problems. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed:

1. A patient therapy and monitoring system comprising:
    at least one implanted device in a patient;
    a home monitoring system in data communication with said at least one implanted device;
    means for providing visual and verbal feedback to the patient integrated with said home monitoring system; and
    a remote expert station in a bi-directional data communication with said at least one implanted device and said home monitoring system, wherein said home monitoring system is configured to receive and process multiple inputs, and said multiple inputs include lifestyle information.

2. The system of claim 1 wherein said at least one implanted device continuously provides patient data to said home monitoring system.

3. The system of claim 1, wherein said multiple inputs include environmental information.

4. The system of claim 1 wherein said means for providing visual and verbal feedback includes a patient notification based on physician treatment plan.

5. The system of claim 1, wherein the at least one implanted device comprises one of: a pacemaker, an insertable loop recorder (ILR), a defibrillator, a cardioverter, a drug pump, a neurostimulator, a hemodynamic monitor.

6. A system according to claim 1, wherein the means for providing verbal and visual feedback is configured to provide information regarding a suggested treatment or therapy plan designed by the patient's physician to promote life style changes intended to positively affect one of: the patient's disease onset, the patient's disease progression, the patient's associated medical problems.

7. A patient therapy and monitoring system comprising:
    at least one implanted device in a patient;
    a home monitoring system in data communication with said at least one implanted device;
    means for providing visual and verbal feedback to the patient integrated with said home monitoring system; and
    a remote expert station in a bi-directional data communication with said at least one implanted device and said home monitoring system, wherein said home monitoring system is configured to receive and process multiple inputs and wherein said multiple inputs include food data stored in a storage system in data communications with said home monitoring system.

8. A system according to claim 7, wherein the at least one implanted device comprises one of: a pacemaker, an insertable loop recorder (ILR), a defibrillator, a cardioverter, a drug pump, a neurostimulator, a hemodynamic monitor.

9. A system according to claim 7, wherein the means for providing verbal and visual feedback is configured to provide information regarding a suggested treatment or therapy plan designed by the patient's physician to promote life style changes intended to positively affect one of: the patient's disease onset, the patient's disease progression, the patient's associated medical problems.

10. A patient therapy and monitoring system comprising:
    at least one implanted device in a patient;
    a home monitoring system in data communication with said at least one implanted device;
    means for providing visual and verbal feedback to the patient integrated with said home monitoring system; and
    a remote expert station in a bi-directional data communication with said at least one implanted device and said home monitoring system, wherein said home monitoring system is configured to receive and process multiple inputs and wherein said inputs include patient manual entry of information pertaining to the patient's health.

11. A system according to claim 10, wherein the at least one implanted device comprises one of: a pacemaker, an insertable loop recorder (ILR), a defibrillator, a cardioverter, a drug pump, a neurostimulator, a hemodynamic monitor.

12. A system according to claim 10, wherein the means for providing verbal and visual feedback is configured to provide information regarding a suggested treatment or therapy plan designed by the patient's physician to promote life style changes intended to positively affect one of: the patient's disease onset, the patient's disease progression, the patient's associated medical problems.

* * * * *